United States Patent [19]

Minobe et al.

[11] Patent Number: 5,588,746
[45] Date of Patent: Dec. 31, 1996

[54] APPARATUS FOR THERMAL ANALYSIS

[75] Inventors: Masao Minobe, Tsuchiura; Noboru Shiraga, Tsukuba; Nobutaka Nakamura, Gotenba, all of Japan

[73] Assignees: Sumitomo Chemical Company, Limited, Osaka; Seiko Instruments, Inc., Tokyo, both of Japan

[21] Appl. No.: 277,046

[22] Filed: Jul. 19, 1994

[30] Foreign Application Priority Data

Jul. 22, 1993 [JP] Japan .................... 5-181639

[51] Int. Cl.$^6$ .................... G01N 25/00; G01N 5/00; G01N 25/20
[52] U.S. Cl. .................... 374/10; 374/12; 374/14; 374/31; 374/45
[58] Field of Search .................... 374/10, 208, 12, 374/14, 31, 45

[56] References Cited

U.S. PATENT DOCUMENTS

| | | | |
|---|---|---|---|
| 3,292,417 | 12/1966 | Hayden et al. | 374/14 |
| 3,373,598 | 3/1968 | Johnson et al. | 374/14 |
| 3,469,455 | 9/1969 | Iwata | 374/14 |
| 3,902,354 | 9/1975 | Harlan et al. | 374/14 |
| 4,763,536 | 8/1988 | Beshoory | 374/14 |
| 5,055,264 | 10/1991 | Czarnecki | 374/14 |
| 5,224,775 | 7/1993 | Reading et al. | 374/11 |

FOREIGN PATENT DOCUMENTS

| | | | |
|---|---|---|---|
| 0044849 | 3/1985 | Japan | 374/14 |
| 63-139239 | 6/1988 | Japan . | |
| 0219540 | 9/1989 | Japan | 374/14 |
| 0875267 | 10/1981 | U.S.S.R. | 374/14 |

OTHER PUBLICATIONS

Carel, A. B., "Modification of the DuPont 1200 °C DTA Cell To Permit the Use of a Variety of Purgegases During Analysis", Laboratory Practice, vol. 24, No. 4, p. 243 (Apr. 1975).

Brevsou, O. et al., "An Apparatus for Automatic Thermogravimetry", Industrial Laboratory, vol. 39, No. 10, p. 1669 (Oct. 1973).

*Primary Examiner*—Diego F. F. Gutierrez
*Attorney, Agent, or Firm*—Birch, Stewart, Kolasch & Birch, LLP

[57] ABSTRACT

In order to carry out thermal analysis under various kinds of atmospheres, there is provided an apparatus for thermal analysis containing a sample chamber having a portion for a sample and a signal detection chamber provided with a signal detection member, the signal detection chamber having an inlet port for a purging gas, the sample chamber and the signal detection chamber being connected through a purging gas passage, and the sample chamber being provided with an inlet port for an atmosphere gas and also with an outlet port for the atmosphere gas and the purging gas.

8 Claims, 8 Drawing Sheets

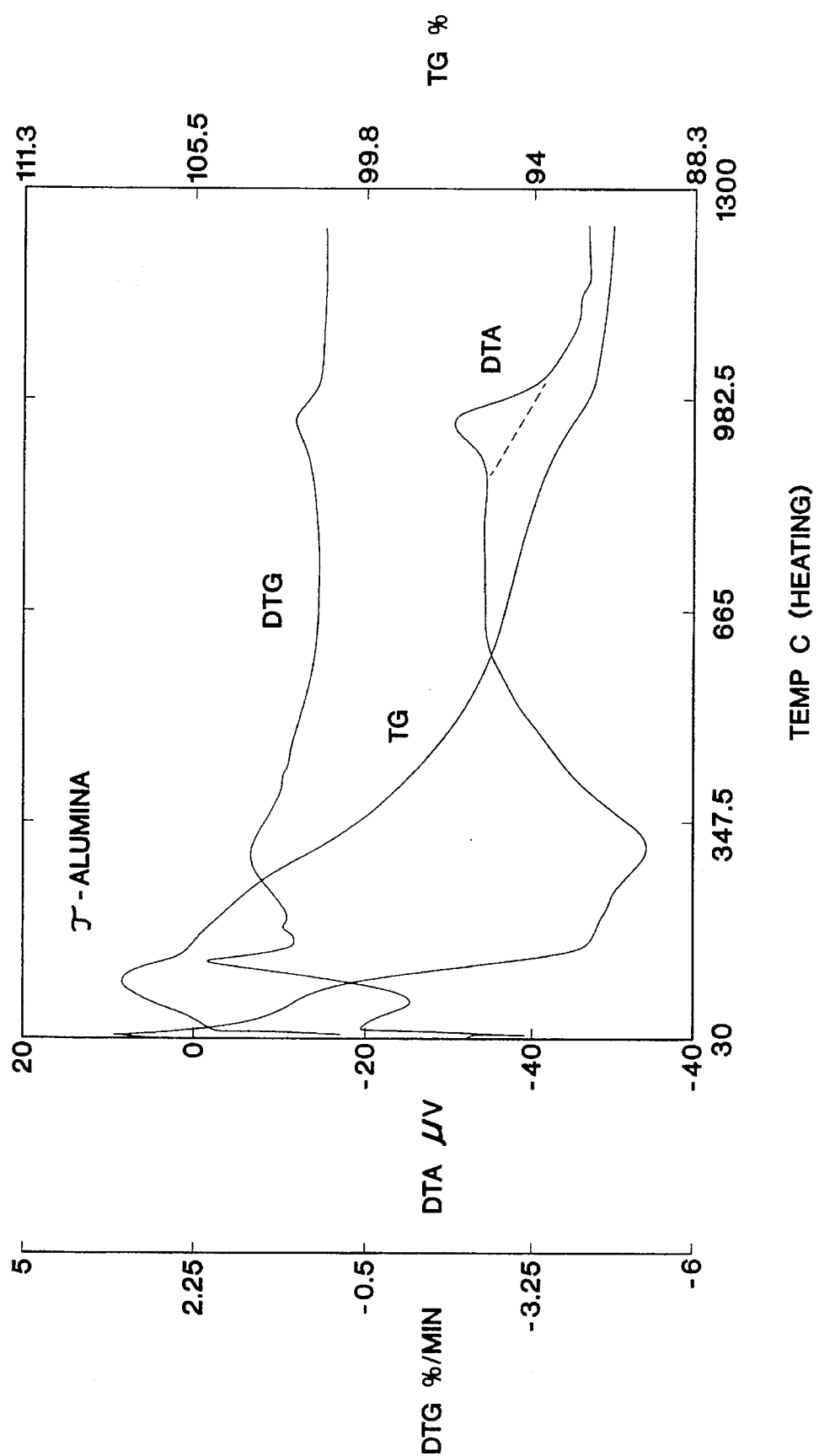

1

APPARATUS FOR THERMAL ANALYSIS

BACKGROUND OF THE INVENTION

1. Field of the Invention

The present invention relates to an apparatus for thermal analysis. Particularly, the present invention relates to an improved apparatus for thermal analysis which makes it possible to carry out thermally analytical measurement under an atmosphere comprising various kinds of gases such as a corrosive gas, a reactive gas and so on, which has been conventionally difficult or otherwise impossible.

2. Description of the Related Art

Thermal analysis has often been used in the fields of material analysis and product quality control because of its versatility and ease of measurement operations as well as the cost of the apparatus for the analysis being lower than that of other types of analytical apparatuses. Thus, thermal analysis has played an important role in both research and production activities.

Thermal analysis, as herein used, is intended to mean any analytical method in which a change of a structure and/or a physical property of a sample is detected under a regulated temperature condition. For example, differential thermal analysis (DTA), thermogravimetry (TG), differential scanning calorimeter analysis (DSC), evolved gas analysis (EGA) and so on are known as thermal analyses.

Among the above analyses, DTA and TG have been most popularly used. An apparatus which carries out a concurred TG-DTA analysis is also commercially available. Recently, an apparatus for TG-DTA analysis is often combined with a mass spectrometer (MS) so that function of EGA is additionally provided. The TG-DTA-EGA function is an extremely convenient and effective analytical method since an emitted gas from the sample as well as a heat balance and a weight change of a sample can be checked during a single measurement run.

By the way, thermal behavior of a sample during the thermal analysis thereof is closely related to the atmosphere which surrounds the sample. For example, when carbon is heated in the air, carbon dioxide is produced while an amount of heat is generated due to an oxidation reaction. However, when carbon is heated in an atmosphere of an inert gas such as nitrogen or helium, neither the production of carbon dioxide nor the heat generation occurs. Therefore, diagrams of the TG or the DTA measurements differ between an atmosphere of air and in that of inert gas.

Particularly, a weight change measured with TG reflects absorption of the atmosphere gas (optionally through a reaction) into the sample or gasification of a portion of the sample. Thus, with TG, the atmosphere surrounding the sample affects the results of measurement more severely than with the other thermal analyses.

Therefore, it is desirable that the thermal analysis be carried out in various atmospheres for the purpose of material research or obtaining product safety data as well as for the purpose of product quality control, However, a thermal analysis apparatus now commercially available is limited in its application to an atmosphere comprising air, nitrogen and so on, and it has been extremely difficult or otherwise impossible to use such an apparatus in other atmospheres comprising a corrosive gas such as chlorine gas.

The thermal analysis apparatus generally comprises a portion for the sample and a portion for signal detection. Since these portions are connected together, the atmosphere gas in the portion for the sample easily goes into the portion for the signal detection due to, for example, diffusion of the gas. When the corrosive gas is used as the atmosphere gas, the portion for the signal detection is damaged by the gas since such a portion is so sensitive to the gas, so that the measurement with the thermal analysis may become impossible.

In order to overcome the above problem, development of a thermal analysis apparatus has been carried out which allows thermal analysis under an atmosphere comprising corrosive gas. A structure of such an apparatus is schematically shown in FIG. 2 which shows a cross sectional view thereof. The apparatus (11) is constructed on the basis of an idea that an inert gas which flows from the portion for the signal detection (14) to the portion for the sample (12) is used as a carrier gas which carries the corrosive gas toward the portion for the sample (12). An inlet port of the inert gas (18) and an inlet port of the corrosive gas (17) are provided for the portion for the signal detection. However, since it is difficult to completely prevent back flow of the corrosive gas toward the portion for the signal detection in such a structure, an extremely large amount of the inert gas should be supplied so as to prevent back flow. Thus, it is substantially impossible to carry out thermal analysis under an atmosphere comprising a concentrated corrosive gas, which means that the apparatus cannot be multi-purpose, and there is a great bar against a multi-purpose apparatus.

As described above, thermal analysis is advantageous in that it is easy to carry out thermal analysis and and a variety of information is obtained, as well as the fact that the apparatus for thermal analysis is relatively inexpensive. Therefore, when thermal analysis can be carried out in the atmosphere comprising a corrosive gas, a reactive gas, an organic gas, a toxic gas and so on as well as in an atmosphere such as air which has been conventionally used, a great deal of advantage would be expected in the research and the production of the product.

SUMMARY OF THE INVENTION

It is, therefore, an object of the present invention to overcome the above problem and to provide an improved apparatus for thermal analysis which allows for thermal analysis under an atmosphere even comprising at least one of a corrosive gas, a reactive gas, an organic gas, a toxic gas and any other gas substantially without any damage to the apparatus due to the atmosphere, such as for example corrosion damage.

According to the present invention, there is provided an apparatus for thermal analysis comprising a sample chamber having a portion for a sample to be analyzed at which the sample is placed and a signal detection chamber provided with a signal detection member which detects a physical change and/or a chemical change of the sample during the thermal analysis characterized in that:

the signal detection chamber comprises an inlet port through which a purging gas is supplied into the signal detection chamber, a partition member having a passage through which the purging gas passes is provided between the sample chamber and the signal detection chamber so as to separate the sample chamber from the signal detection chamber, and the sample chamber is provided with an inlet port through which an atmosphere gas is supplied into the sample chamber so that the sample is subjected to a predeter-

BRIEF DESCRIPTION OF THE DRAWINGS

FIG. 8 shows a graph in which results of TG-DTA measurement of Example 5 are indicated.

DETAILED DESCRIPTION OF THE INVENTION

In a preferred embodiment of the apparatus for thermal analysis according to the present invention, the sample chamber and the signal detection chamber are located horizontally and coaxially with respect to each other in their positional relationship.

In another preferred embodiment of the apparatus for thermal analysis according to the present invention, the inlet port for the atmosphere gas provided in the sample chamber is located upstream of the portion for the sample with respect to a flowing direction of the purging gas.

In a further embodiment of the apparatus for thermal analysis according to the present invention, the partition member is so constructed that a ratio of a cross sectional area of the purging gas passage (A) to a cross sectional area of the partition member (including the passage) (B) which is adjacent to the sample chamber on one side thereof and also to the signal detection chamber on the other side thereof, namely a ratio of A/B, is preferably not larger than ½ and not smaller than 1/100, and more preferably not larger than 1/10 and not smaller than 1/100.

In a further embodiment of the apparatus for thermal analysis according to the present invention, the atmosphere gas comprises at least one selected from a corrosive gas and a reactive gas.

No other gas but the purging gas can substantially flow into the signal detection chamber since the signal detection chamber is almost completely separated from the sample chamber by the partition member having the purging gas passage and a pressure in the signal detection chamber is kept higher during the measurement than that in the sample chamber because of the supply of the purging gas through the inlet port. That is, even though a concentrated corrosive gas is supplied as the atmosphere gas, the gas does not substantially flow back into the signal detection chamber so that the signal detection chamber is not heavily damaged by the gas.

As described above, it is preferable that the sample chamber and the signal detection chamber are located horizontally. By aligning the two chambers horizontally, flows of both gases (i.e. the atmosphere gas and the purging gas) hardly affect signals to be detected (especially weight signals).

In addition, the inlet port for the atmosphere gas is located enough upstream of the portion for the sample in the sample chamber with respect to the flow direction of the purging gas stream so as to ensure that the sample is fully exposed to the atmosphere gas.

DESCRIPTION OF THE PREFERRED EMBODIMENTS

The present invention will be, hereinafter, described with reference to the accompanying drawings.

Figure 1:
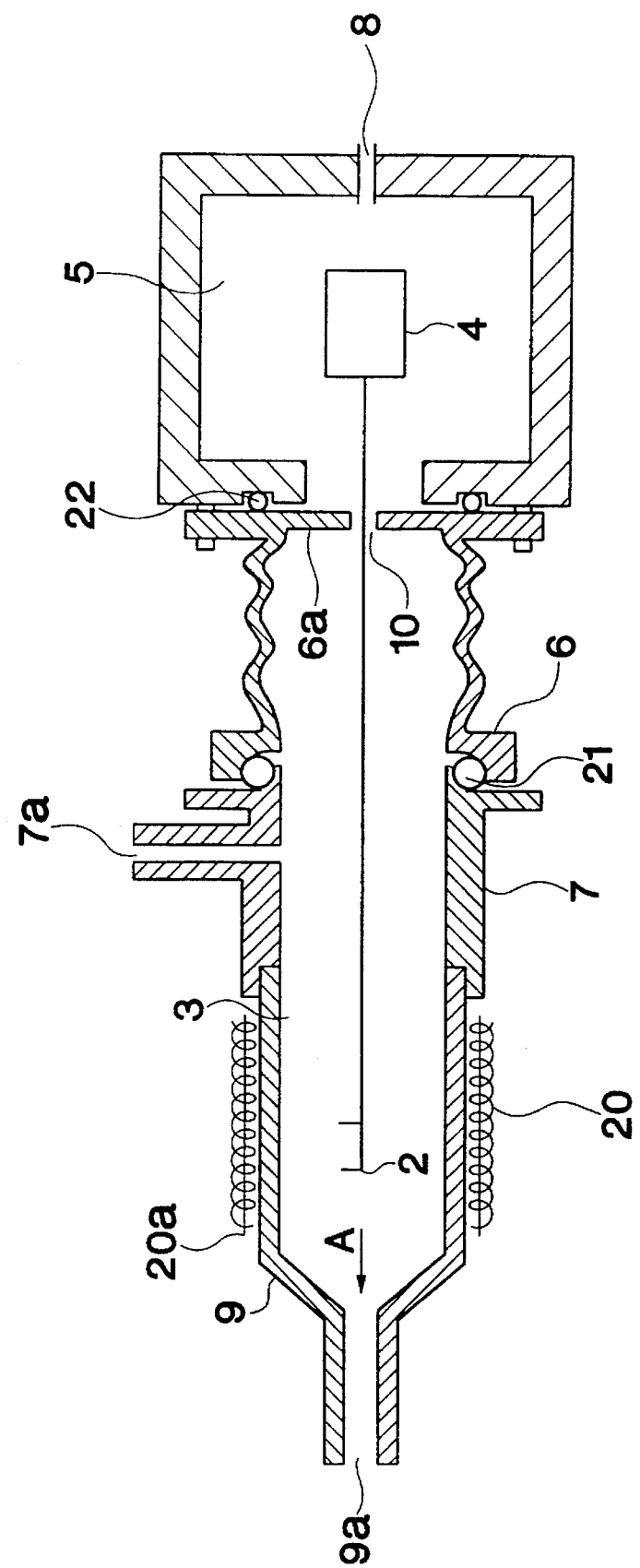
FIG. 1 schematically shows a cross sectional view of an apparatus for thermal analysis according to the present invention.
Figure 2:
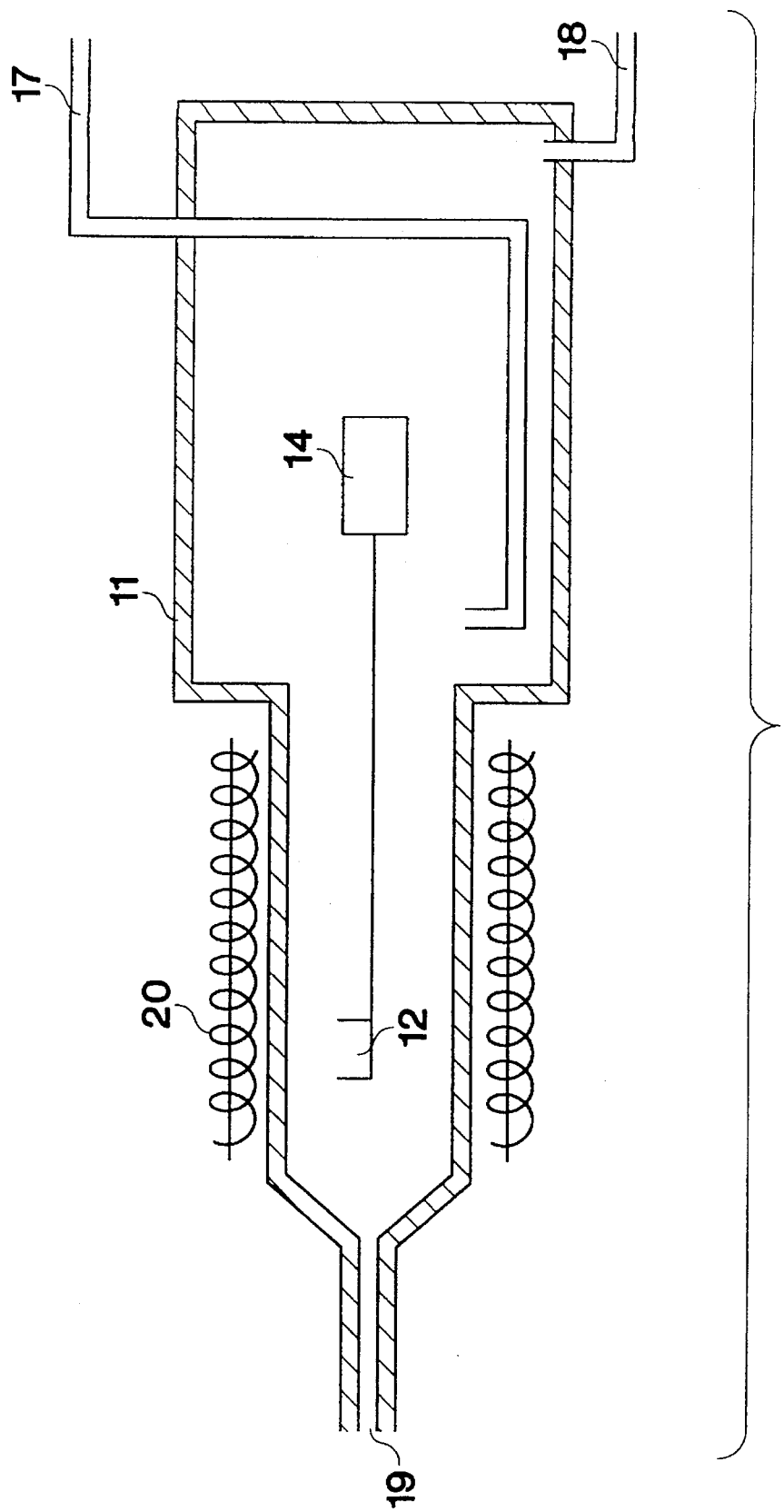
FIG. 2 schematically shows a cross sectional view of an apparatus for thermal analysis of the prior art.

FIG. 1 schematically shows a cross sectional view of the apparatus for thermal analysis according to the present invention. The apparatus (1) is of a type for a so-called thermogravimetry (TG) which measures a weight (thus, a weight change) of a sample as function of temperature or a time. Though the present invention will be explained as to the TG apparatus, it should be noted that the present invention is also applicable to other thermal analysis apparatuses similar to the TG apparatus. The sample chamber (3) in which the portion for the sample (2) is located so as to place the sample thereon is constructed as follows:

The sample chamber (3) is enclosed by a furnace tube (9) made of a sintered alumina in the form of a cylinder having, at one end of the tube, an outlet port (9a) through which the atmosphere gas and the purging gas are withdrawn, a connection tube (7) made of a stainless steel having, on its side surface, an inlet port (7a) through which the atmosphere gas is supplied into the sample chamber and engaging, at one end thereof, with the other end of the furnace tube (9), and a bellows member (6) which is disconnectablly connected, at one end thereof, with the other end of the connection tube (7) through an O-ring (21).

The furnace tube (9), the connection tube (7) and the bellows member (6) are so located that their cylindrical axes are aligned substantially co-axially and preferably horizontally one another.

The partition member (6a) is provided at the other end of the bellows member (6), and the signal detection chamber (5) having the portion for the signal detection (4) is located over the partition member (6a) through an O-ring (22) so as to measure a change of a physical quantity or quantities of the sample. The partition member (6a) separates the sample chamber (3) from the signal detection chamber (5). The partition member (6a) comprises a purging gas passage (10) through which the purging gas flows from the signal detection chamber (5) to the sample chamber (3). The purging gas passage (10) allows the purging gas to pass therethrough and also a signal of the physical quantity to be transferred to the portion for the signal detection (4). Concretely, the passage is generally a hole which is preferably located around a center of the partition (thus, the center is aligned with the both chambers). A shape of the hole is not specifically limited, and it may be for example circular, oval, square and rectangular. It is of course possible to provide a plurality of the purging gas passages (10) for the partition member (6a). The physical quantity to be detected is, for example, a temperature of the portion for the sample (2) or of the sample itself measured by a thermo-couple, a weight of the sample measured by a balance beam or the like, and the signal to be transferred corresponds to such a physical quantity. The signal is sent to the portion for the signal detection (4) in the signal detection chamber (5) and the thermal analysis is carried out.

A heating member (20) is located around an outer periphery of the furnace tube (9). The heating member (20) comprises a bobbin made of a sintered alumina (20a) around which a platinum-rhodium (80:20) wire is wound non-dielectrically. The heating member (20) heats the portion for the sample (2) through the furnace tube (9) so that a temperature of the portion may be changed between a room temperature and, for example, 1500° C.

The inlet port (8) of the purging gas is provided for the signal detection chamber (5) so as to supply the purging gas into the chamber (5). In order to thermally analyze the sample under a predetermined atmosphere, the atmosphere gas is supplied to the sample chamber (3) through the inlet port (7a) of the atmosphere gas. The purging gas supplied to the signal detection chamber (5) flows into the sample chamber (3) through the purging gas passage (10). The purging gas and the atmosphere gas in the sample chamber (3) are withdrawn through the outlet port (9a) to the outside.

The inlet port (7a) of the atmosphere gas is located upstream of the portion for the sample in the sample camber (3) with respect to the flow direction of the purging gas. Thus, the atmosphere gas supplied to the sample chamber (3) and the purging gas are both heated by the heating member (20) to a temperature substantially equal to that of the portion for the sample (2) in the sample chamber (3) while they travel toward the portion (2). The outlet port (9a) through which the purging gas and the atmosphere gas are withdrawn is located at an end tip of the sample chamber (3) downstream of the portion for the sample with respect to the flow direction of the purging gas, and the both gases flow along a direction of an arrow A as shown in FIG. 1 (namely, from right hand to left hand) without forming stagnation of the gases.

When the sample is placed on or removed from the portion for the sample (2), the heating member (20), the furnace tube (9) and the connection tube (7) which are substantially integral are separated from the cylindrical bellows member (6) and moved to a left hand direction (namely, along the direction indicated by the arrow A) so as to expose the portion (2). After the sample is placed or removed, the integral members (20), (9) and (7) are again connected with the bellows member (6).

Generally, there are two types of the thermal analysis apparatuses such as a thermobalance with respect to their positional relationship of the sample chamber and the signal detection chamber; one is of a vertical type in which those two chambers are vertically located in series, and the other is of a horizontal type in which those two chambers are horizontally located in series.

In the vertical type apparatus, since the gas flows along a vertical (namely, gravitative) direction around the portion for the sample (2), the streams of the purging gas and/or the atmosphere gas affect the weight measurement so that measurement accuracy gets worse. In addition, a so-called chimney effect also affects the weight measurement.

To the contrary, the above problems do not occur in thermal analysis with the horizontal type apparatus (namely, a horizontal type thermobalance). Therefore, the purging gas can be selected from many kinds of gases and also a flow rate thereof can be selected from a wide range, whereby the diffusion of the atmosphere gas into the signal detection chamber is prevented more easily in the horizontal type thermobalance than in the vertical type thermobalance. Thus, the horizontal type thermobalance is preferable for easily achieving the object of the present invention.

The partition member which separates the sample chamber from the signal detection chamber functions to prevent the back flow and/or the diffusion of the atmosphere gas into the signal detection chamber. In order to so obtain such a function of the partition member, a ratio of a cross sectional area (A) of the purging gas passage of the partition member to a cross sectional area (B) of the partition member (namely, of a portion which contacts the sample chamber and the signal detection chamber on either side thereof including the cross sectional area of the passage), namely A/B, is preferably not larger than about ½ and not smaller than about 1/100 and more preferably not larger than about 1/10 and not smaller than about 1/100. A material from which the partition member is formed is not specifically limited and any material may be used for the partition member provided that it is heat resistant and also resistant to at least an intended atmosphere gas and preferably to the various kinds of the atmosphere gases. Preferably, the material may be a stainless steel, Monel metal or any other metal material which is chemically resistant against the intended atmosphere gas.

A space composed of the sample chamber (3) and the signal detection chamber (5) is gas tight such that a pressure in the space is easily reduced to a relatively high degree of vacuum such as $10^{-2}$ torr by closing the inlet port of the atmosphere gas (7a) and the inlet port of the purging gas (8) and evacuating the space with a rotary pump through the outlet port (9a). This gas tightness is essentially important so as to accurately control the atmosphere around the portion for the sample (2).

The inlet port of the atmosphere gas (7a) is preferably located upstream from the portion for the sample (2) with respect to the gas flow direction so as to ensure that the supplied atmosphere gas reaches the portion for the sample (2) after it has been heated to a temperature substantially equal to a temperature of the portion for the sample (2) or the sample itself.

In addition, a material of which the inlet port of the atmosphere gas (7a) is made is extremely important, and selection of such a material should be carried out under consideration of sufficient mechanical strength and sufficient heat resistance in addition to sufficient chemical resistance against an intended atmosphere gas in order to ensure a performance and safety of the apparatus. Concretely, a stainless steel, Monel metal and other metal materials may be used for the inlet port depending on the intended atmosphere gas.

Also, it is preferable to prevent the back flow of the atmosphere gas into the signal detection chamber by slightly reducing a pressure in the side of the purging gas flowing away (namely, in the sample chamber) relative to a pressure in the signal detection chamber. A gas withdrawn through the gas outlet port comprises the atmosphere gas, the purging gas and a generated gas if any, and the withdrawn gas is generally vented to outside after a treatment thereof for harmlessness.

Any gas may be used as the atmosphere gas depending on an object for the thermal analysis in which the present apparatus is used. Such a gas is not specifically limited, and for example, a corrosive gas (such as hydrogen chloride, hydrogen iodide, hydrogen bromide, hydrogen fluoride, chlorine, iodine, bromine, fluorine and sulfurous gas), a reactive gas (such as hydrogen, oxygen, steam, ammonia, carbon monoxide and an organic gas), a toxic gas and so on may be used.

The purging gas used is also not specifically limited provided that it does not damage the thermal analysis apparatus due to, for example, corrosion and that it meets the object of the thermal analysis. For example, an inert gas such as nitrogen, helium and the like or air may be used as the purging gas.

Though concrete thermal analysis operations using the present apparatus as described above will be explained in detail with reference to Examples, it should be understood that those Examples do not limit the scope of the present invention at all.

EXAMPLE 1

A TG/DTA thermal analysis apparatus commercially available from Seiko Instruments Inc., Tokyo, Japan (Model 320) was reconstructed to have an apparatus as shown in FIG. 1 which comprises the partition member (6a) between the sample chamber (3) and the signal detection chamber (5). The partition member was made of a stainless steel. The ratio of the cross sectional area of the purging gas passage (A) to the cross sectional area of the partition member (B) (which corresponds to an area of a surface contacting the sample chamber and the signal detection chamber), namely A/B, was about 1/3.

Figure 3:
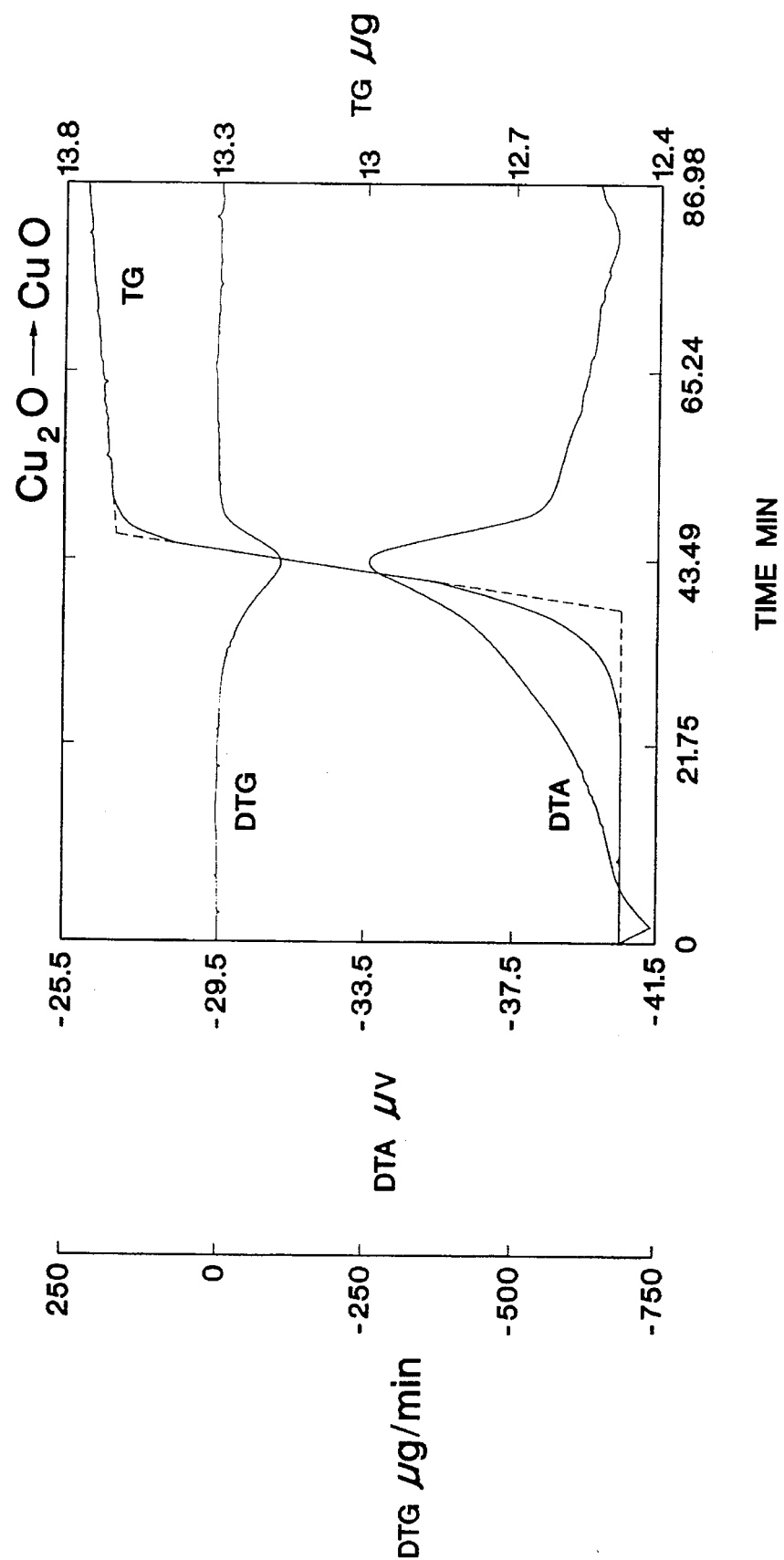
FIG. 3 shows a graph in which results of TG-DTA measurement of Example 1 are indicated.

Using the apparatus as described above, behavior of an oxidation reaction was analyzed. Cuprous oxide ($Cu_2O$, 10.4 mg) was used as a sample. Oxygen gas was supplied at a flow rate of 30 ml/min. as the atmosphere gas and helium was supplied at a flow rate of 100 ml/min. as the purging gas. Results of the TG-DTA measurement which show the behavior of the oxidation reaction are shown in FIG. 3.

The oxidation reaction of $Cu_2O$ to $CuO$ is clearly seen from the results of the thermal analysis. By using oxygen gas as the atmosphere gas, the measurement was easily and accurately carried out without any degradation of performance of the apparatus. After the measurement, the apparatus was inspected and no damage was found due to the corrosion.

EXAMPLE 2

Figure 4:
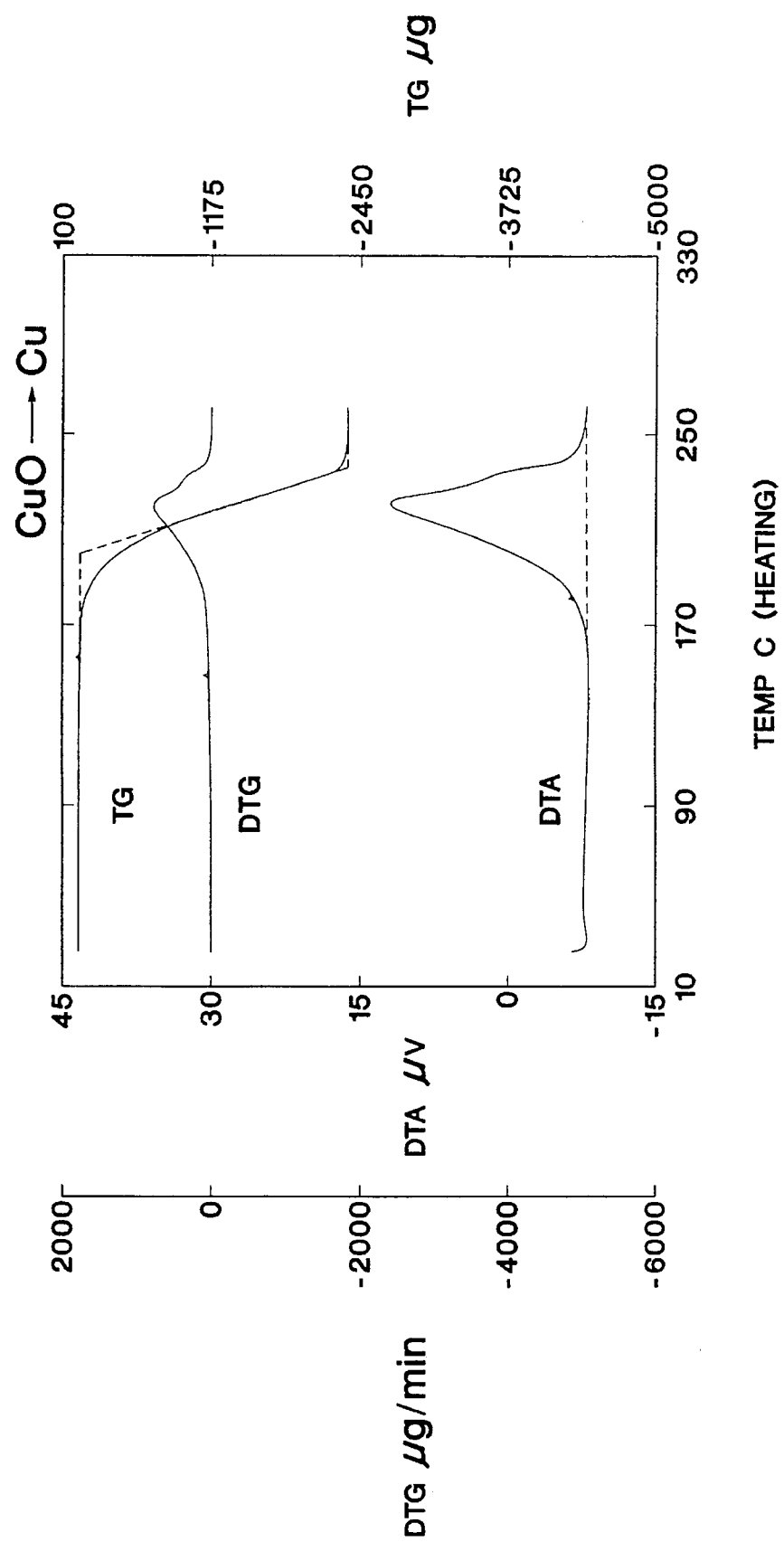
FIG. 4 shows a graph in which results of TG-DTA measurement of Example 2 are indicated.

Using the apparatus of Example 1, behavior of a reduction reaction of cupric oxide (CuO, 13.5 mg) was analyzed. Hydrogen was supplied at a flow rate of 80 ml/min. as the atmosphere gas and helium was supplied at a flow rate of 110 ml/min. as the purging gas. Results of the TG-DTA measurement which show the behavior of the reduction reaction are shown in FIG. 4. It is seen from the results that analysis of the reduction reaction can be carried out accurately. In addition, it is confirmed that the thermal analysis can be carried out easily and safely even when hydrogen gas is used. No degradation of the performance of the thermal analysis apparatus occurred. Further, when the apparatus was inspected after the measurement, no damage was found.

EXAMPLE 3

Figure 5:
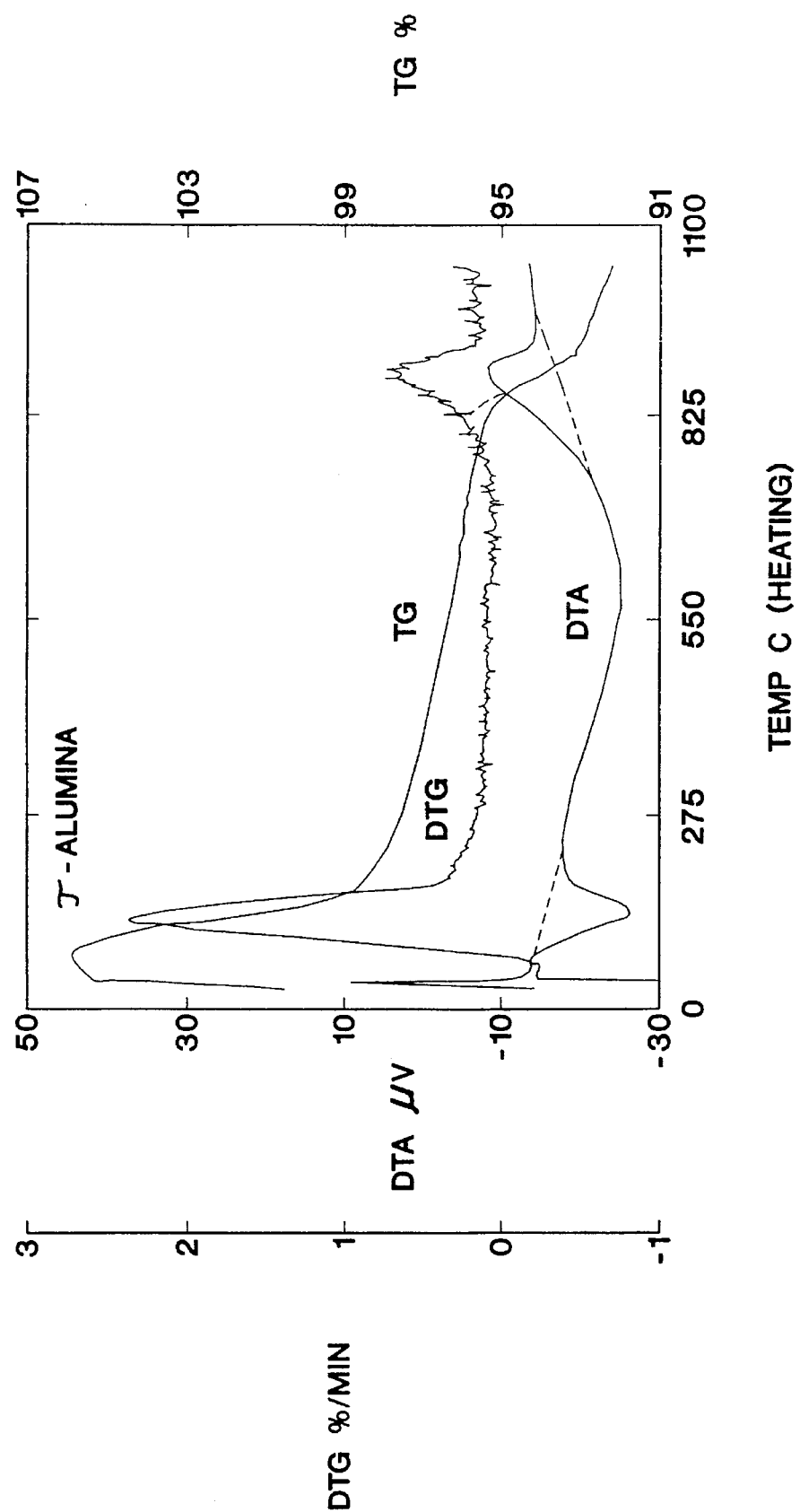
FIG. 5 shows a graph in which results of TG-DTA measurement of Example 3 are indicated.

Using the apparatus of Example 1, behavior of a transition alumina under an atmosphere comprising hydrogen chloride gas (a flow rate of 100 ml/min.) was analyzed. The transition alumina was used in an amount of 11.2 mg. Nitrogen was supplied at a flow rate of 100 ml/min. as the purging gas. A temperature of the atmosphere in which the behavior was observed was increased at a rate of 20° C./min. Results of the TG-DTA measurement are shown in FIG. 5. It is seen from the results that the transition alumina was unstable under the atmosphere comprising hydrogen chloride gas. In addition, it is confirmed that the thermal analysis can be carried out easily and accurately even when the corrosive gas such as hydrogen chloride gas is used. Further, when the apparatus was inspected after the measurement, no damage was found.

EXAMPLE 4

A TG/DTA thermal analysis apparatus commercially available from Seiko Instruments Inc., Tokyo, Japan (Model 320) was reconstructed to have an apparatus as shown in FIG. 1 which comprises the partition member (6a) between the sample chamber (3) and the signal detection chamber (5). The partition member was made of a stainless steel. The ratio the cross sectional area of the purging gas passage (A) to the cross sectional area of the partition member (B) (which corresponds to an area of a surface contacting the sample chamber and the signal detection chamber), namely A/B, was about 1/20.

Figure 6:
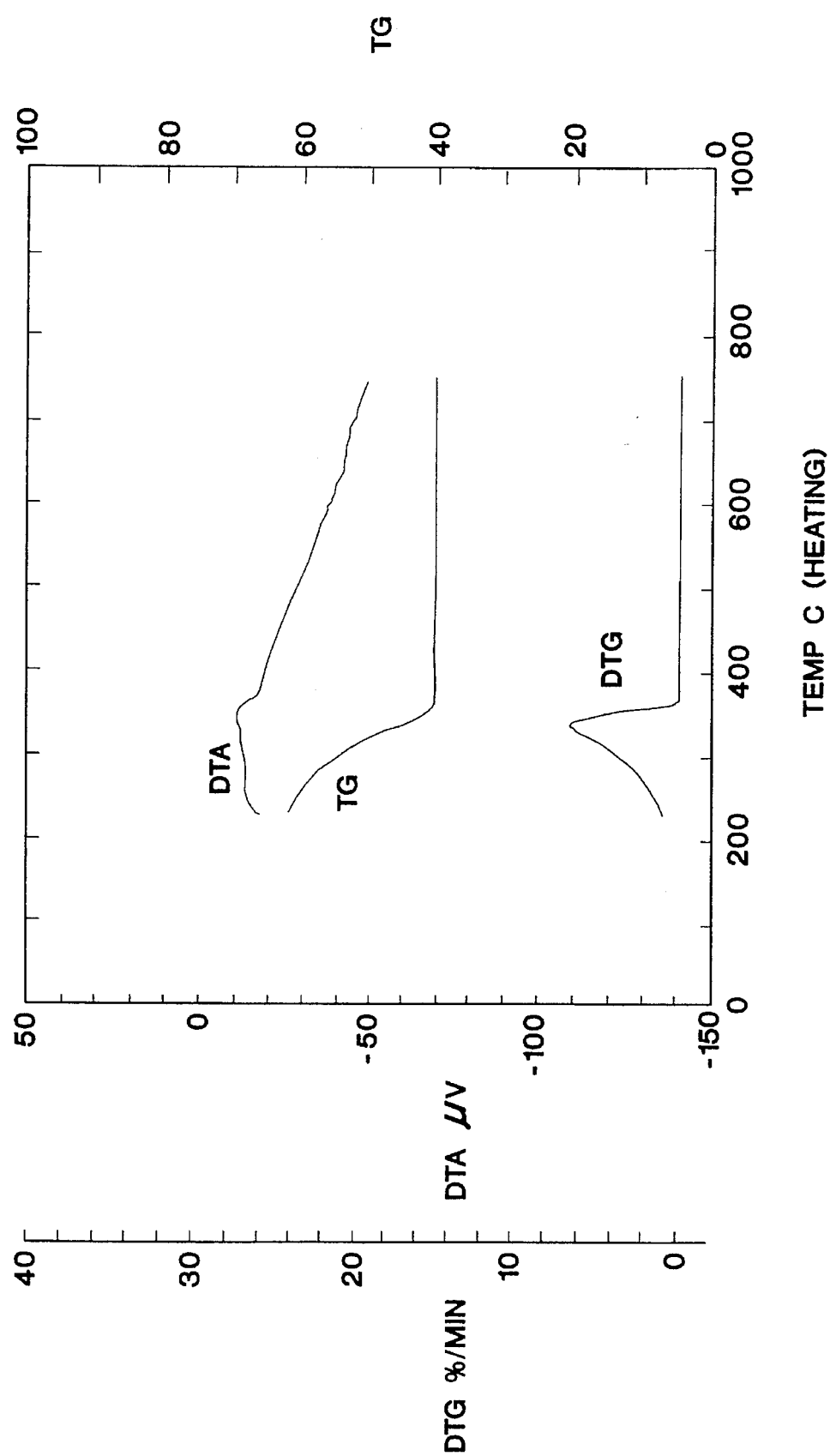
FIG. 6 shows a graph in which results of TG-DTA measurement of Example 4 are indicated.

An additional heating member was wound around the connection tube (7) and the inlet port of the atmosphere gas (7a) in the thermal analysis apparatus, and steam was supplied through the inlet port (7a) into the sample chamber (3) at a pressure of 488 mmHg as the atmosphere gas while a temperature in the inlet port (7a) was kept at 100° C. Nitrogen was supplied through the inlet port (8) as the purging gas at a flow rate of 200 ml/min. TG-DTA measurement of ferrous chloride ($FeCl_2 \cdot nH_2O$, about 25 mg) was carried out with a temperature increasing rate of 20° C./min. Results of the measurement are shown in FIG. 6.

Figure 7:
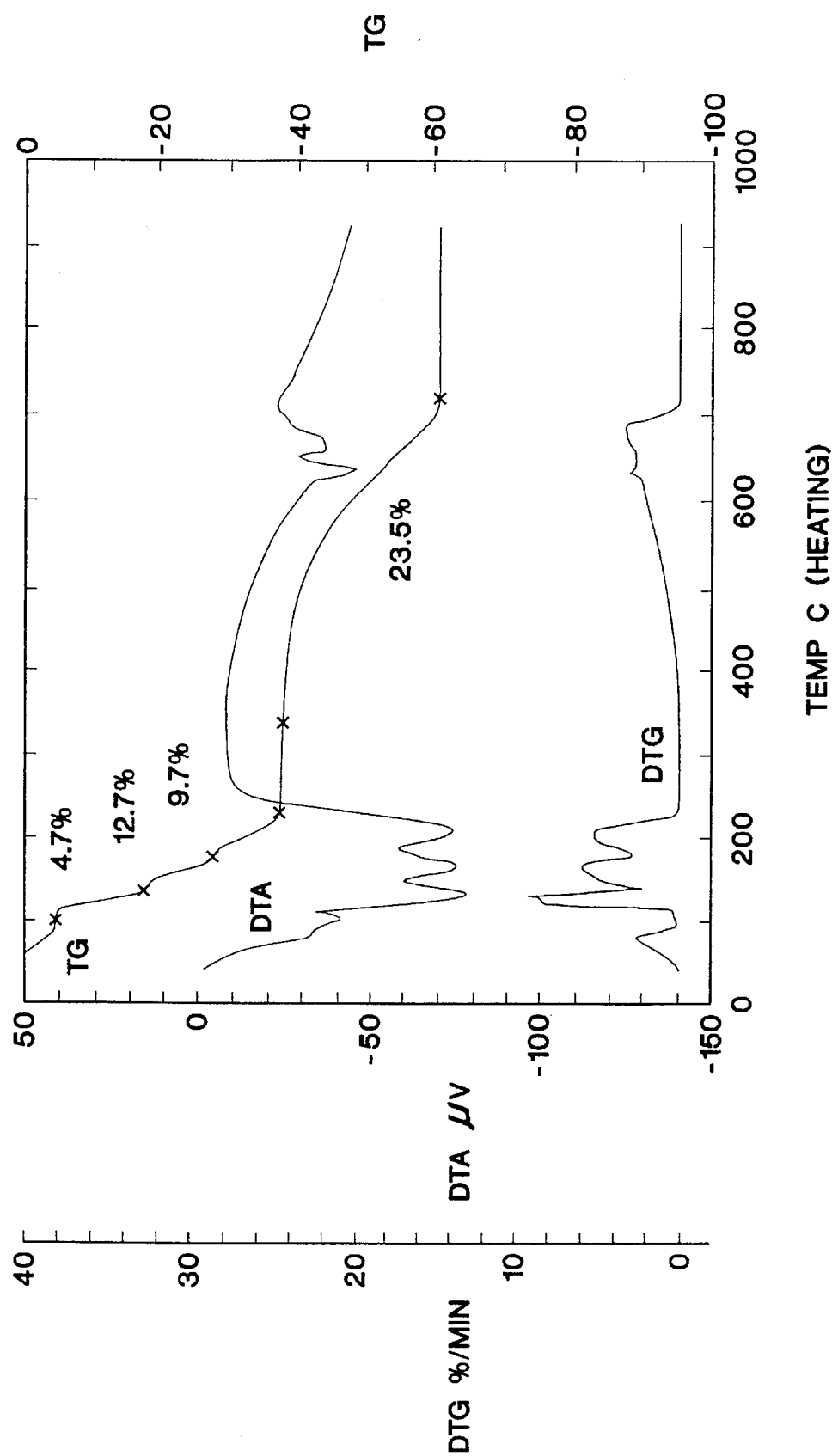
FIG. 7 shows a graph in which results of TG-DTA measurement obtained by an apparatus of the prior art are indicated.

On the other hand, the inlet port of the atmosphere gas (7a) was closed to stop the steam supply. While only nitrogen was supplied through the inlet port (8) at a flow rate of 200 ml/min., TG-DTA measurement with respect to the same sample was carried out conventionally with increasing the temperature at a rate of 20° C./min. Results are shown in FIG. 7.

In the conventional analysis where the steam was not supplied, a four step dehydration reaction was observed at a temperature below 200° C. and a weight of the sample was decreased over a wide range of from 400° to 700° C. (see FIG. 7). To the contrary, in the case where the steam was supplied, the weight of the sample decrease was completed within a narrow range of from 250° to 350° C. and data were obtained which confirmed that heat resistance of ferrous chloride was degraded in the presence of the steam of 488 mmHg (see FIG. 6). It is seen from these results that the thermal analysis can be carried out easily and accurately even in the presence of the steam. After the measurement, the apparatus was checked and no corrosion was found.

EXAMPLE 5

A TG/DTA thermal analysis apparatus commercially available from Seiko Instruments Inc., Tokyo, Japan (Model 320) was reconstructed to have an apparatus as shown in FIG. 1 which comprises the partition member (6a) between the sample chamber (3) and the signal detection chamber (5). The partition member was made of a stainless steel and two purging gas passages were provided in the partition member. The ratio of the total cross sectional area of the two purging gas passages (A) to the cross sectional area of the partition member (B) (which corresponds to an area of a surface contacting the sample chamber and the signal detection chamber), namely A/B, was about 1/5.

Using the apparatus, behavior of a transition alumina was observed under hydrogen iodide at a flow rate of 50 ml/min. An amount of the transition alumina was 69.6 mg and nitrogen gas was supplied at a flow rate of 100 ml/min. as the purging gas. The temperature of the atmosphere around the alumina was increased at a rate of 30° C./min. Result of the TG-DTA measurement are shown in FIG. 8. It is seen from the results that the transition alumina is unstable under the atmosphere of hydrogen iodide. In addition, it is confirmed that the thermal analysis can be carried out easily and accurately even when the corrosive gas such as hydrogen iodide gas is used. Further, when the apparatus was inspected after the measurement, no damage was found with the apparatus. The above measurement was repeated many times and no damage was found and stable measurement results were obtained.

By using the apparatus for the thermal analysis according to the present invention, it has become possible for the first time to carry out the thermal analysis easily and surely under the atmosphere comprising any gas such as the corrosive gas and the reactive gas without any damage to the apparatus due to the atmosphere gas, for example, corrosion. Other various applications of the present apparatus may be contemplated. For example, the apparatus may be typically used for the measurement of thermal properties of various kinds of materials under the atmosphere comprising various kinds of gases. Another application is chemical reaction analysis of various kinds of materials.

What is claimed is:

1. An apparatus for thermal analysis comprising a sample chamber having a portion for a sample to be analyzed at which the sample is placed and a signal detection chamber provided with a signal detection member which detects a physical change or a chemical change in the sample during the thermal analysis, wherein the signal detection chamber comprises an inlet port through which a purging gas is supplied into the signal detection chamber, a partition member having a passage through which the purging gas passes is provided between the sample chamber and the signal detection chamber so as to separate the sample chamber from the signal detection chamber, and the sample chamber is provided with an inlet port through which an atmosphere gas is supplied into the sample chamber so that the sample is subjected to a predetermined atmosphere comprising the atmosphere gas, and the sample chamber is provided with an outlet port through which the atmosphere gas and the purging gas are withdrawn to the outside of the apparatus, wherein the partition member is so constructed that a ratio of a cross sectional area of the purging gas passage (A) to a cross sectional area of the partition member (B) which is adjacent to the sample chamber on one side thereof and also to the signal detection chamber on the other side thereof is not larger than $\frac{1}{2}$ and not smaller than $\frac{1}{100}$.

2. The apparatus according to claim 1 wherein the atmosphere gas comprises at least one selected from a corrosive gas and a reactive gas.

3. The apparatus according to claim 1 wherein the sample chamber and the signal detection chamber are located horizontally and coaxially with respect to each other in the positional relationship thereof.

4. The apparatus according to claim 1 wherein the inlet port for the atmosphere gas provided in the sample chamber is located upstream of the portion for the sample with respect to a flowing direction of the purging gas.

5. An apparatus for thermal analysis comprising a sample chamber having a portion for a sample to be analyzed at which the sample is placed and a signal detection chamber provided with a signal detection member which detects a physical change or a chemical change in the sample during the thermal analysis, wherein the signal detection chamber comprises an inlet port through which a purging gas is supplied into the signal detection chamber, a partition member having a passage through which the purging gas passes is provided between the sample chamber and the signal detection chamber so as to separate the sample chamber from the signal detection chamber, and the sample chamber is provided with an inlet port through which an atmosphere gas is supplied into the sample chamber so that the sample is subjected to a predetermined atmosphere comprising the atmosphere gas, and the sample chamber is provided with an outlet port through which the atmosphere gas and the purging gas are withdrawn to the outside of the apparatus, wherein the partition member is so constructed that a ratio of a cross sectional area of the purging gas passage (A) to a cross sectional area of the partition member (B) which is adjacent to the sample chamber on one side thereof and also to the signal detection chamber on the other side thereof is not larger than $\frac{1}{10}$ and not smaller than $\frac{1}{100}$.

6. The apparatus according to claim 5 wherein the atmosphere gas comprises at least one selected from a corrosive gas and a reactive gas.

7. The apparatus according to claim 5 wherein the sample chamber and the signal detection chamber are located horizontally and coaxially with respect to each other in the positional relationship thereof.

8. The apparatus according to claim 5 wherein the inlet port for the atmosphere gas provided in the sample chamber is located upstream of the portion for the sample with respect to a flowing direction of the purging gas.

* * * * *